United States Patent [19]

Miraki

[11] Patent Number: 5,318,535
[45] Date of Patent: Jun. 7, 1994

[54] LOW-PROFILE DUAL-LUMEN PERFUSION BALLOON CATHETER WITH AXIALLY MOVABLE INNER GUIDE SHEATH

[75] Inventor: Manouchehr Miraki, Aliso Viejo, Calif.

[73] Assignee: Baxter International Inc., Deerfield, Ill.

[21] Appl. No.: 80,266

[22] Filed: Jun. 21, 1993

[51] Int. Cl.⁵ ............................................ A61M 29/00
[52] U.S. Cl. ................................... 604/102; 128/898
[58] Field of Search ............................. 604/96–102; 128/898

[56] References Cited

U.S. PATENT DOCUMENTS

| | | | |
|---|---|---|---|
| 4,581,017 | 4/1986 | Sahota | 604/101 |
| 4,813,934 | 3/1989 | Engelson et al. | 604/99 |
| 4,820,349 | 4/1989 | Saab | 128/344 |
| 4,877,031 | 10/1989 | Conway et al. | 604/96 |
| 4,944,745 | 7/1990 | Sogard et al. | 606/194 |
| 4,955,895 | 9/1990 | Sugiyama et al. | 606/194 |
| 4,988,356 | 1/1991 | Crittenden et al. | 606/192 |
| 4,990,138 | 2/1991 | Bacich et al. | 604/96 |
| 5,035,686 | 7/1991 | Crittenden et al. | 604/96 |
| 5,047,945 | 9/1991 | Arney et al. | 606/194 |
| 5,087,247 | 2/1992 | Horn et al. | 604/98 |
| 5,090,960 | 2/1992 | Michael | 604/101 |
| 5,100,381 | 3/1992 | Burns | 604/96 |
| 5,104,399 | 4/1992 | Lazarus | 623/1 |
| 5,120,323 | 6/1992 | Shockey et al. | 604/282 |
| 5,137,513 | 8/1992 | McInnes et al. | 604/96 |
| 5,147,377 | 9/1992 | Sahota | 606/194 |
| 5,154,725 | 10/1992 | Leopold | 606/194 |
| 5,160,321 | 11/1992 | Sahota | 604/96 |
| 5,163,903 | 11/1992 | Crittenden et al. | 604/96 |

FOREIGN PATENT DOCUMENTS

| | | |
|---|---|---|
| 93887A | 4/1982 | European Pat. Off. ...... A61M 1/03 |
| 212159A | 3/1987 | European Pat. Off. . |
| 378178A | 7/1990 | European Pat. Off. . |
| 381062A | 8/1990 | European Pat. Off. . |
| 406901A | 1/1991 | European Pat. Off. . |
| WO9222342 | 12/1992 | European Pat. Off. ..... A61M 25/00 |
| 3036192 | 9/1980 | Fed. Rep. of Germany . |
| 3314755A | 8/1984 | Fed. Rep. of Germany . |

*Primary Examiner*—Jerome L. Kruter
*Attorney, Agent, or Firm*—Poms Smith Lande & Rose

[57] ABSTRACT

A fully exchangeable low-profile dual-lumen perfusion balloon catheter for dilatation angioplasty procedures includes a flexible small diameter guide wire in a perfusion lumen of the catheter and is provided with an internal guide wire sheath member traversing the dilatation balloon and allowing full perfusion blood flow via this lumen when the guide wire and sheath member are retracted. When the guide wire and sheath together are advanced from their retracted positions, the sheath member positively prevents escape of the guide wire distal end from the catheter lumen via the perfusion ports thereof. Another embodiment of the invention includes a guide wire sheath member with a smaller size pilot dilatation balloon and a valving structure responsive to axial relative movement of the guide wire to allow inflation of this pilot balloon in response to communication of pressurized fluid to the guide wire sheath member at a proximal end thereof. Still another alternative embodiment of the inventive catheter includes a guide wire and guide wire sheath member which are in one operative relationship axially relatively movable and telescopically received one within the other. In another operative relationship of the guide wire and guide wire sheath member, the two are axially aligned and coupled at adjacent ends to provide an extended guide structure allowing removal of the balloon catheter and retracing of the vascular path to the area of treatment. Another alternative embodiment of the inventive catheter is configured with a mono-rail distal guide portion.

22 Claims, 4 Drawing Sheets

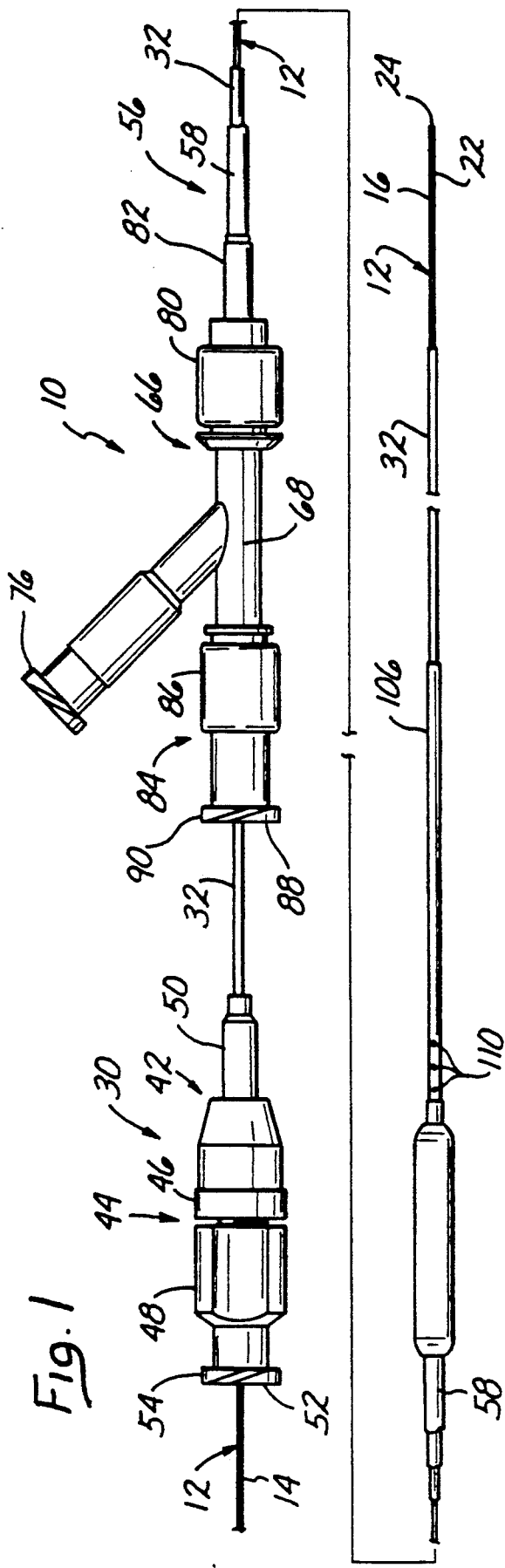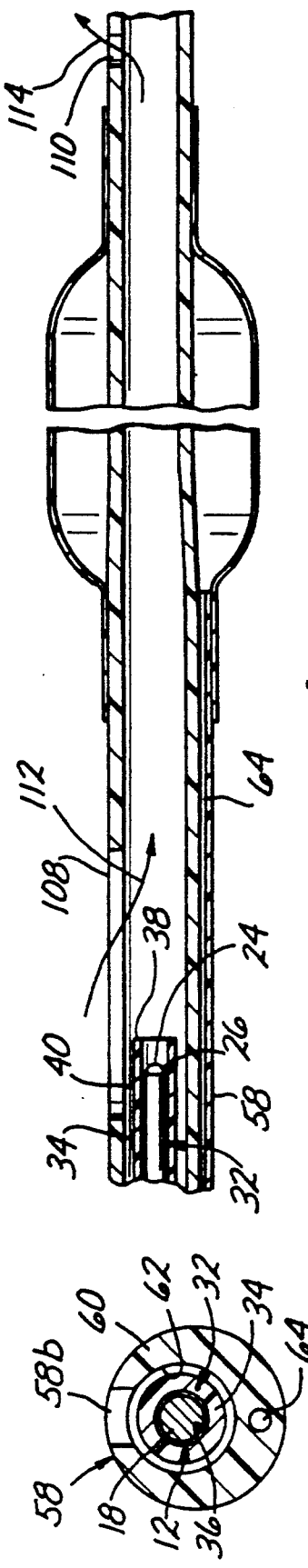
Fig. 1
Fig. 3
Fig. 4

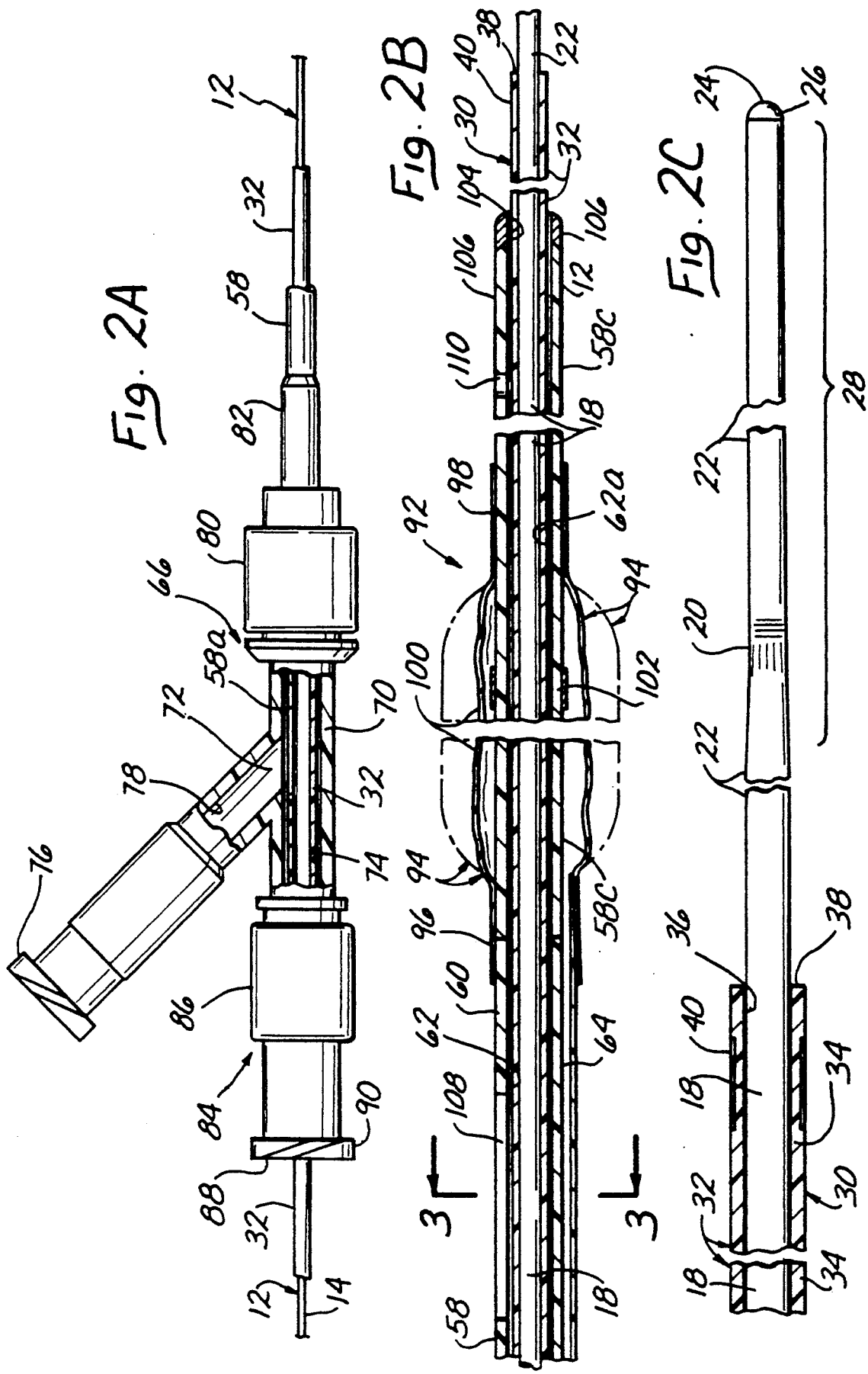

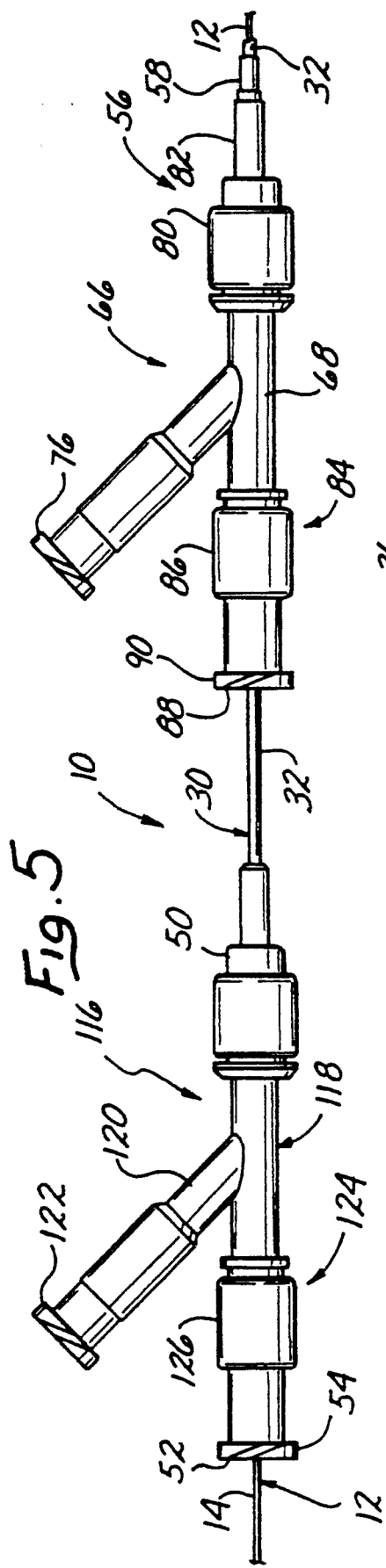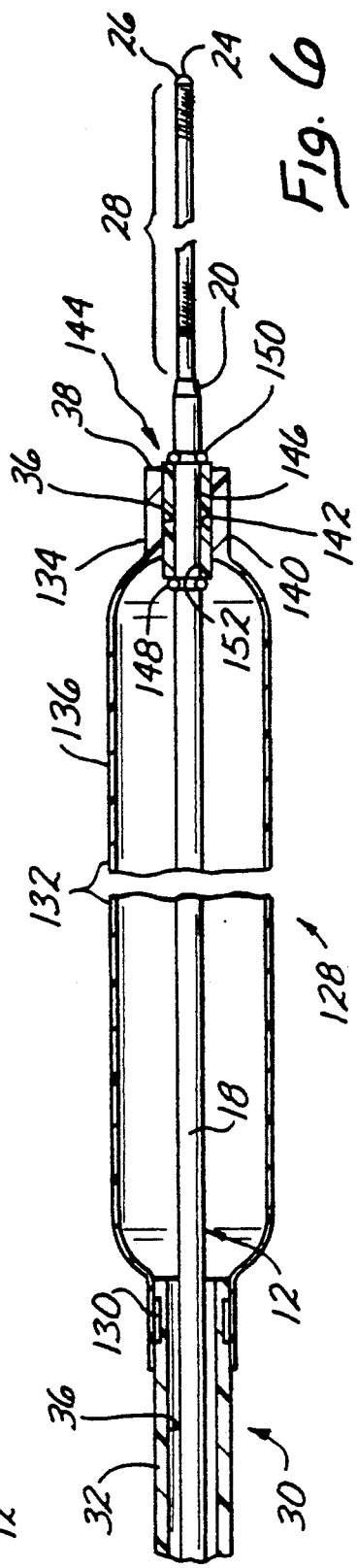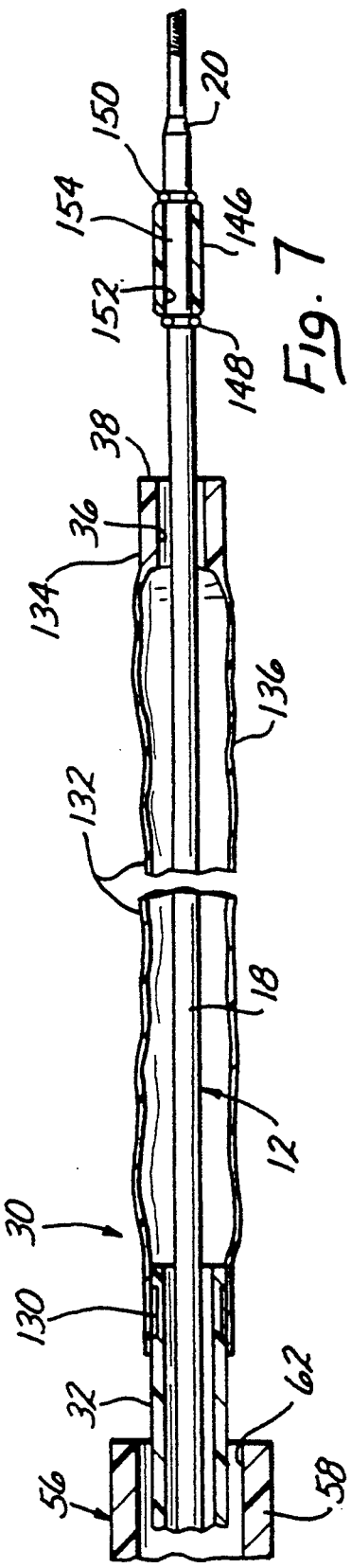

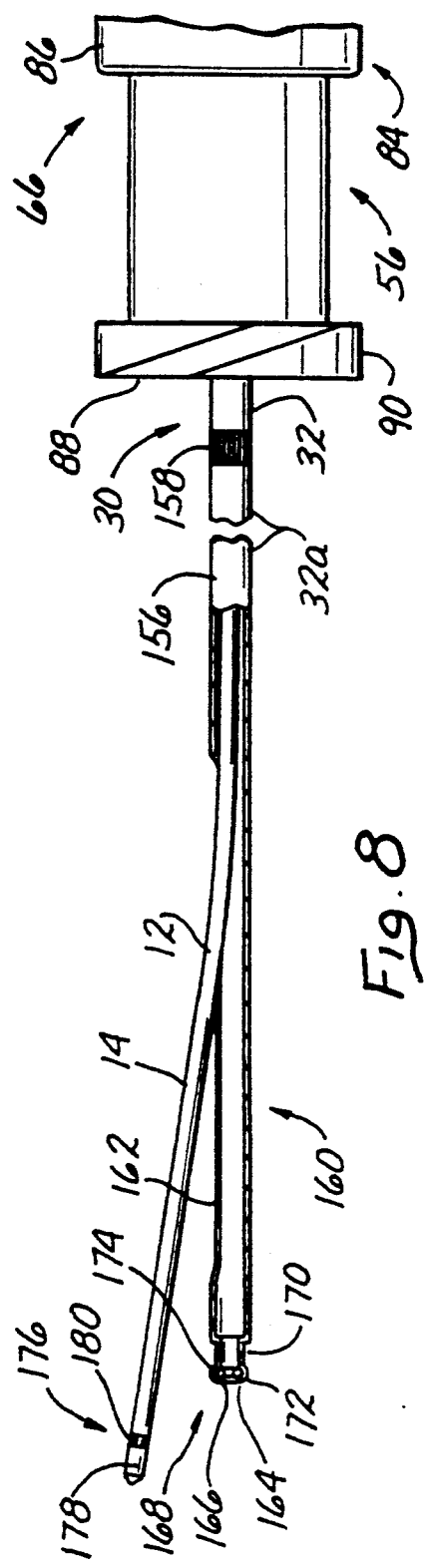
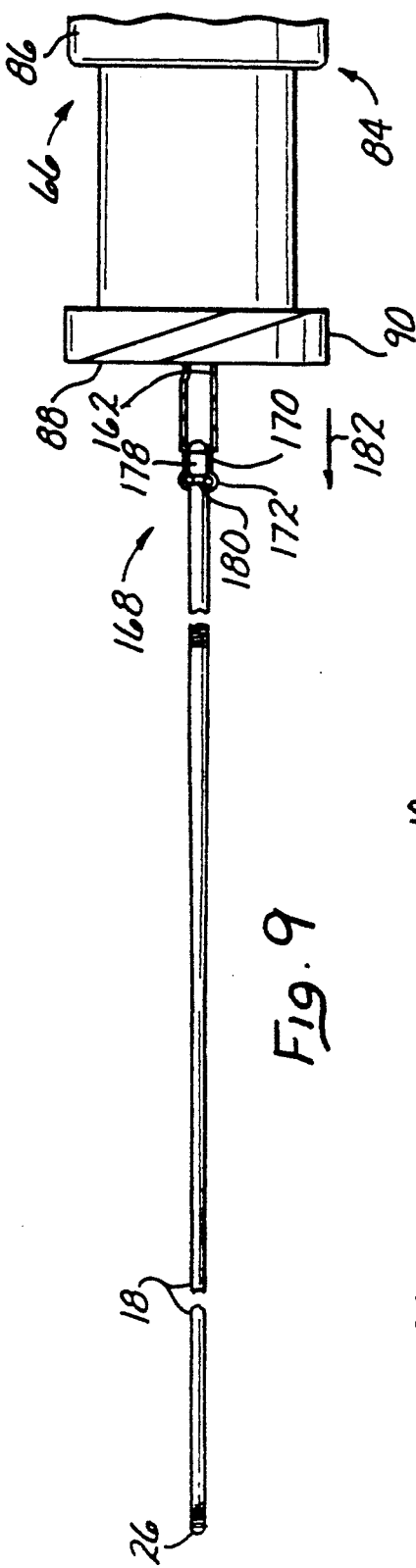
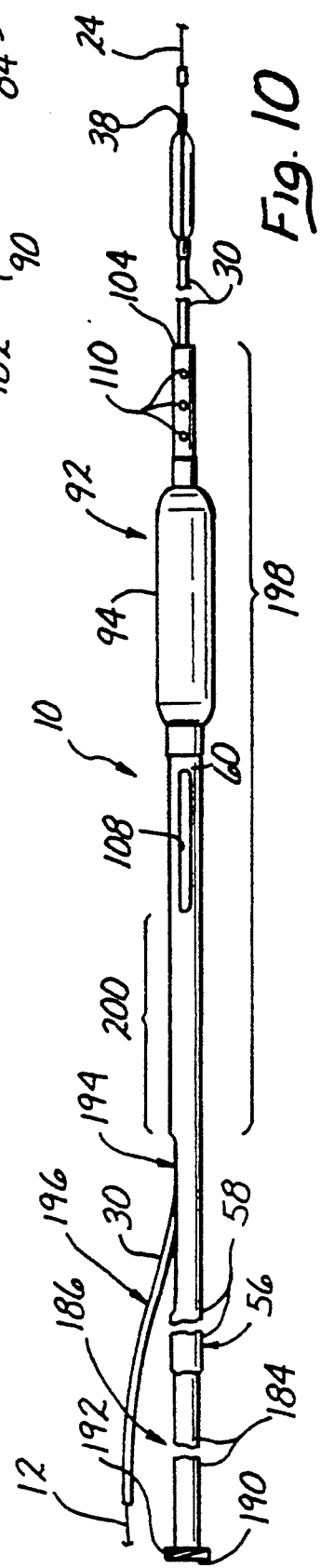

LOW-PROFILE DUAL-LUMEN PERFUSION BALLOON CATHETER WITH AXIALLY MOVABLE INNER GUIDE SHEATH

BACKGROUND OF THE INVENTION

1. Field of the Invention

The present invention relates in general to the field of dilatation or balloon catheters employed in the treatment of vascular diseases. More particularly, the present invention relates to a dual-lumen low-profile balloon catheter assembly with perfusion ports communicating proximally and distally of the dilatation balloon via a lumen of the catheter. An axially movable inner guide sheath receives a guide wire assembly for the catheter. Distal ends of the guide sheath and guide wire are movable across the perfusion ports in the proximal direction to allow blood perfusion flow through the full cross sectional area of the catheter lumen. When the guide sheath is moved across the perfusion ports in the distal direction it allows the distal end of the guide wire to traverse these ports with no possibility that the wire end will escape through these ports, improving patient safety.

2. Related Technology

Over the past decade the medical procedure known as angioplasty has become widely accepted as a safe and effective method for treating various types of vascular diseases. For example, angioplasty is widely used for opening stenoses throughout the vascular system and particularly for opening stenoses in coronary arteries.

At present, the most common form of angioplasty is called percutaneous transluminal coronary angioplasty (PTCA). This procedure utilizes a dilatation catheter having an inflatable balloon at its distal end. By using a fluoroscope and radiopaque dyes and markers on the catheter for visualization the distal end of the dilatation catheter is guided into position through a guide catheter and across the stenosis. With the dilatation balloon is in this position of alignment with the stenosis the balloon is inflated for a brief duration to open the artery and establish adequate blood flow.

Typically, inflation of the balloon is accomplished by supplying pressurized fluid from an inflation apparatus located outside the patient's body through an inflation lumen in the catheter which communicates with the balloon. Conversely, applying a negative pressure to the inflation lumen collapses the balloon to its minimum dimension for initial placement or for removal of the balloon catheter from within the blood vessel receiving treatment.

In the past years a number of balloon catheter designs have been developed which have contributed to the safety and acceptability of PTCA and similar medical procedures. The most common design is known as an "over-the-wire" balloon catheter. This conventional device typically utilizes a relatively large lumen for passage of a guide wire and injection of contrast fluid (or angiographic visualization dye) to assist in the placement of the device. A second parallel lumen is provided for inflation and deflation of the balloon.

Typically, a steerable guide wire is positioned within the larger lumen and the entire assembly is maneuvered into an initial position within the target artery through a guide catheter which has been positioned previously, and which is of sufficient diameter to pass the angioplasty catheter. Once near the site of the stenoses the guide wire can be rotated and axially extended or retracted into position across the lesion. The therapeutic angioplasty catheter is subsequently advanced along the guide wire to position its balloon end portion across the lesion prior to inflation of the balloon and dilatation of the stenosis.

An alternative conventional over-the-wire catheter assembly utilizes a non-removable guide wire that allows for longitudinal or axial movement. However, this design has a significant drawback because the entire catheter assembly with its non-removable guide wire must be removed to accomplish replacement or exchange of the balloon. In some cases of PTCA it is necessary to replace the balloon with one of different diameter or configuration following the initial dilatation.

However, cases of acute reclosure have been noted where the lesion closes again following dilatation and removal of the balloon catheter. One response to this reclosure problem has been the placement of an expandable stent into the artery at the lesion with another replacement balloon catheter. This alternative system increases the difficulties of these subsequent procedures by requiring that the replacement catheter renegotiate the entire placement path without the advantage of a guide wire.

A "monorail" variant of the standard balloon-over-a-wire system also has been developed in which only the distal portion of the balloon catheter tracks over the guide wire. This system utilizes a conventional inflation lumen and a relatively short guiding or through lumen adjacent to the distal end of the catheter. Principal benefits of the monorail construction of therapeutic catheter are the reduction of frictional drag over the length of the externally located guide wire and the ease of balloon exchange. This construction provides the ability to recross an acutely closed vessel or to exchange balloons without removing the guide wire.

However, a disadvantage of this "mono-rail" design is the increased difficulty in steering the guide wire because the guide wire is not supported by the balloon catheter. Also, the balloon catheter itself may not be pushable to move along the guide wire. Some versions of the monorail use an external flexible pusher member which also tracks the guide wire and is used to move the therapeutic catheter to the desired location near the distal end of the guide wire. Additionally, the dual lumen distal design of the monorail catheters produces a larger profile and catheter shaft size.

Another innovation in dilatation catheter design which is now conventional is the "fixed-wire" or integrated "balloon-on-a-wire" dilatation catheter. These single lumen designs utilize a relatively narrow wire positioned within the inflation lumen and permanently fixed to the distal end of the balloon. This construction produces a low-profile catheter assembly which is able to cross severely narrowed lesions and to navigate tortuous vascular pathways. Additionally, the fixed guide wire bonded at the distal end of the balloon improves the steerability and pushability of these designs which enhances their maneuverability. The thin shaft design also improves coronary visualization and enables all but the tightest critical lesions to be crossed.

However, though able to provide relatively quick and simple balloon placement as well as providing access to lesions otherwise unsuitable for PTCA, fixed-wire balloon-on-a-wire systems sacrifice the ability to maintain guide wire position across the lesion when exchanging balloons or the safety advantage of being able to recross an acutely closed vessel without repositioning the entire assembly.

Yet another difficulty arises when the dilatation balloon is inflated to dilate the vessel under treatment. While this balloon is inflated blood cannot circulate in the vessel. This lack of blood circulation can lead to necrosis of tissues already stressed by the previously reduced level of blood flow. As a solution to this problem, catheters have been provided with perfusion ports proximal and distal to the balloon and communicating with one another via a lumen of the catheter which extends through the balloon.

A conventional catheter of this type is known from U.S. Pat. No. 4,581,017, issued 8 Apr. 1986 to H. Sahota. This catheter includes a dual or multi lumen flexible shaft with a dilatation balloon carried on the shaft. Perfusion ports proximally and distally of the dilatation balloon allow perfusion blood flow.

A conventional catheter of this latter type is also depicted in U.S. Pat. No. 5,160,321, issued 3 Nov. 1992, to H. Sahota. The catheter depicted in the Sahota patent employs a separate inner lumen to outwardly bound an annular axially extending passage through which blood may flow past the inflated balloon via perfusion ports. Also, this separate inner lumen inwardly defines a passage through which the guide wire assembly for the catheter extends.

However, with catheters of the type illustrated by the Sahota patent, and others of this type, the distal portion of the catheter is obstructed by the guide wire, or by the guide wire and its lumen. Consequently, the cross sectional area of the catheter lumen which is available for blood perfusion past the inflated balloon is very limited. While the distal end portion of the catheter may be made of a size sufficient to pass an adequate volume of blood, this size increase is contrary to the recognized advantages of having a low-profile catheter.

Alternatively, it has been proposed to withdraw the guide wire proximally of the perfusion ports prior to inflation of the dilatation balloon in order to make a larger part of the perfusion lumen available for blood flow. However, a serious disadvantage arises when the guide wire is again advanced in that the distal tip of the guide wire may inadvertently pass outwardly of the catheter through one of the perfusion ports. The Sahota patent recognizes the risk of this possibility, and provides the inner guide wire lumen as a partial and not completely satisfactory solution to this problem.

SUMMARY OF THE INVENTION

Accordingly, in view of the recognized deficiencies of conventional catheters discussed above, it is an object of the present invention to provide a dual-lumen perfusion balloon dilatation catheter which includes a guide wire and perfusion lumen, and which during inflation of the balloon and circulation of patient blood through the guide wire and perfusion lumen makes all of the cross sectional area of this lumen available for perfusion blood flow.

An additional object for the present invention is to provide such a catheter with an internal guide wire guide sheath which is axially movable across the perfusion ports of the catheter, and is of a diameter too large to pass through these ports. Thus, the guide wire and guide sheath can be withdrawn proximally of the perfusion ports to allow the entire cross sectional area of the guide wire and perfusion lumen to flow perfusion blood. Subsequently, the guide sheath and guide wire may be advanced across the perfusion ports with no risk of the guide wire distal end escaping from this lumen through the perfusion ports. Once past distally of the perfusion ports, the comparatively smaller diameter guide wire can be used to cross tight lesions and to conventionally guide the advancement of the catheter.

It is an additional object of the present invention to provide a dual-lumen perfusion balloon catheter of the above-described character offering an extremely low profile and a small shaft size to facilitate maneuverability and placement of the catheter as well as to provide the catheter with the ability to negotiate tortuous vessels and to pass highly stenosed lesions.

An additional object is to provide a dual-lumen catheter of the above-described character in which the guide sheath itself carries a pilot dilatation balloon of a smaller size than the balloon carried by the catheter shaft. This pilot dilatation balloon is inflatable by cooperation of a valving feature of the guide wire assembly with a valving sleeve portion of the guide sheath to close the distal opening of the guide sheath. Thus, the pilot balloon may be used, for example, to initially dilate a tight lesion in preparation for entry therein of the catheter balloon and further dilatation of the lesion.

Yet another object of the present invention is to provide a dual-lumen catheter of the above-described character wherein the guide sheath and guide wire can be coupled to provide a guide assembly extended sufficiently to allow it to remain in place across a lesion under treatment while the therapeutic catheter is withdrawn in preparation for its replacement at the lesion with another catheter, for example, of a larger balloon size. Thus, the invention will provide the benefits of a small diameter fixed wire system yet allow for removal, reengagement or replacement of the balloon while leaving the guide wire in place to preserve an easily renegotiated path back to and along the blood vessel being treated.

These and other objects of the present invention are achieved by a low-profile dual-lumen perfusion balloon catheter, which in accordance with broad structural aspects thereof, includes at least a dual-lumen catheter with a balloon section, a guide wire and perfusion lumen traversing the balloon section, proximal and distal perfusion ports communicating with one another via the guide wire and perfusion lumen, a guide wire assembly traversing the balloon section, and a guide sheath received in the guide wire and perfusion lumen and receiving the guide wire to traverse the perfusion ports while positively preventing the guide wire distal end portion from escaping the catheter via the perfusion ports.

This unique construction allows removal of the catheter and its replacement with a second or subsequent catheter to perform lesion therapeutic treatment, for example. Thus, trauma to the patient may also be reduced by use of the present catheter. The time required for lesion treatments may also be reduced because the number of catheter replacements required may be reduced or eliminated.

To facilitate visualization of the guide wire and balloon catheter during angioplasty the apparatus of the present invention is preferably provided with one or more radiopaque markers. Typically, these markers are formed of small coils, strips or spheres of gold, platinum, tantalum or other dense, relatively inert metal. In one embodiment of the present invention a radiopaque spring coil of flexible wire is provided proximally to the valving portion of the guide wire assembly. Similarly, a radiopaque marker is located along the shaft of the catheter. When these two markers are disposed in a first axially spaced relative position the single dilatation balloon of the guide sheath is inflatable. When the two markers are moved into a second position of congruence with one another by axial relative movement of the guide wire assembly, the distal vent port is communicated with the single lumen of the guide sheath.

It is also contemplated as being within the scope of the present invention to position radiopaque markers on the balloon catheter to enable the physician to visualize the placement of the balloon relative to the guide wire and stenotic lesion.

Other features and advantages of the present invention will become apparent from the following detailed description of exemplary and preferred embodiments of the invention, taken in conjunction with the accompanying drawings which illustrate, by way of example, the principals of the present invention.

BRIEF DESCRIPTION OF THE DRAWINGS

FIG. 1 presents a fragmentary view in elevation of a low-profile dual-lumen perfusion balloon catheter, with portions of the structure broken away to better depict features of the invention;

FIGS. 2-2C provide enlarged fragmentary cross sectional views of portions of the catheter seen in FIG. 1, each depicted at a progressively larger scale to better depict salient structural features of the invention;

FIG. 3 is an enlarged cross-sectional view taken at line 3—3 of FIG. 2B;

FIG. 4 is a partial longitudinal cross sectional view of the distal portion of the low-profile dual-lumen perfusion balloon catheter seen in FIG. 2B, and shown in an alternative operative configuration;

FIGS. 5 and 6 are respective fragmentary views of proximal and distal end portions of an alternative embodiment of the inventive catheter, which are shown partially in cross section and at progressively enlarged scales like that of portions of FIGS. 2 to better depict features of the invention;

FIG. 7 is an enlarged cross sectional view of the distal end portion of the catheter seen in FIG. 6, and illustrating an alternative deflated-balloon operative position of the catheter;

FIG. 8 is an enlarged fragmentary cross sectional view similar to FIG. 2A, but depicting a proximal portion of yet another alternative embodiment of the inventive catheter;

FIG. 9 presents a fragmentary longitudinal cross sectional view similar to FIG. 8, but illustrating an alternative operative configuration of the components of the catheter; and FIG. 10 presents a fragmentary side-elevation view of another alternative embodiment of the present invention, which is of a mono-rail configuration.

DETAILED DESCRIPTION

Referring more particularly to the drawings in which similar elements are indicated by identical reference numerals, FIG. 1 shows a low-profile dual-lumen perfusion balloon catheter, generally referenced with the numeral 10. In overview, the catheter 10 includes an elongate guide wire assembly, generally indicated with the numeral 12, and extending from end to end through the remainder of the catheter assembly. A proximal end portion 14 of the guide wire assembly 12 is seen in FIG. 1 projecting from a proximal end of the remainder of the catheter 10. Also, a distal end portion 16 of the guide wire assembly 12 is also seen projecting distally from the remainder of the catheter 10.

This guide wire assembly 12 includes a proximal elongate wire-like shaft 18 (best seen in FIGS. 2), which defines the proximal end portion 14, and which extends at a substantially constant diameter distally to a weld 20 (seen in FIG. 2C) at which its diameter is reduced and at which an elongate spring-like portion 22 of the guide wire assembly 12 is secured.

The elongate spring-like portion 22 is received over a reduced diameter portion (not visible in the Figures) of the wire-like shaft portion 18. This reduced diameter portion extends within the spring-like portion 22 to or proximate to the distal end 24 of the guide wire assembly 12. At the end 24, the guide wire assembly is provided with a rounded tip portion 26. The spring-like portion 22, or an external or internal part thereof, may be formed of radiopaque material to define a distal marker for the guide wire assembly 12. Proximally of the tip portion 26, the spring portion 22 includes a portion 28 tapering proximally to a larger diameter approximating the diameter of the shaft portion 18, and providing for introduction of the guide wire assembly and of catheter 10 into tight lesions.

Viewing FIGS. 1 and 2 in conjunction, it is seen that the catheter assembly 10 includes several component parts arranged telescopically around one another and extending axially. As just described, the inner one of these components is the guide wire assembly 12. Next outwardly around the guide wire assembly 12 is a tubular guide wire sheath assembly, generally referenced with the numeral 30. This guide wire sheath assembly 30 includes an elongate flexible tubular shaft 32 having a side wall 34 defining a bore 36 which is open from end to end of the shaft 32 (best seen viewing FIGS. 2, and particularly FIG. 2C). Adjacent to a distal end 38 (seen in FIG. 2C) of the shaft 32, the side wall 34 carries embedded therein a radiopaque marker sleeve 40.

At a proximal end portion 42 (seen in FIG. 1) of the guide wire sheath assembly 30, the assembly includes a guide wire sheath chuck and seal assembly, generally referenced with the numeral 44. This chuck and seal assembly 44 includes first and second threadably engaged portions 46 and 48 which cooperatively form a flare fitting and which sealingly receive between them a flared portion (not visible in the Figures) of a coupling sleeve 50. This coupling sleeve 50 is sealingly joined with the shaft 32. At its proximal end 52, the second portion 48 defines a luer fitting 54 by which fluid may be injected into the guide wire sheath assembly 30, and from which extends the proximal end portion 14 of the guide wire assembly 12.

Catheter assembly 10 also includes an elongate catheter shaft assembly 56. This catheter shaft assembly includes an elongate dual-lumen catheter shaft 58, which is seen in FIGS. 2A, 2B, and 3. The catheter shaft 58 includes a side wall 60 defining a bore 62 which receives the guide wire sheath assembly 30 at the shaft portion 32 thereof. Side wall 60 also defines a comparatively small second balloon inflation lumen 64. At a proximal portion of the catheter shaft assembly 56, the latter includes a Y-fitting 66 with a body 68 having a side wall 70 defining a Y-shaped internal cavity 72 (best seen viewing FIG. 2A). This Y-shaped internal cavity 72 includes a through portion 74 which sealingly receives a portion 58a of the shaft 58.

Shaft portion 58a has a part thereof at 58b cut away to communicate the balloon inflation lumen 64 with the cavity 72. Thus, the balloon inflation lumen 64 is outwardly communicated via a luer fitting 76 and a branch part 78 of the cavity 72. In other words, the body 68 sealingly receives the shaft 58 at a first flare fitting 80 which receives a first coupling sleeve 82 which is joined with the shaft 58. Also, the body 68 sealingly cooperates with the shaft 58 at a second flare fitting 84 in sealingly cooperation with a similar coupling sleeve (not visible in the drawing Figures) also sealingly coupled with the shaft 58 and disposed in the cavity 72. Finally, the second flare fitting 84 includes a fitting nut 86 which at an end 88 thereof defines a luer fitting 90 from which the shaft 32 of the guide wire sheath 30 extends proximally.

Viewing FIG. 2B, it is seen that the shaft 58 at a distal end portion 92 thereof also includes an expansible balloon portion 94 which is sealingly secured to the shaft 58 at proximal and distal bonds 96, 98, respectively. This balloon portion 94 includes a side wall 100, which in the solid line condition of FIG. 2B is deflated and folded or wrapped on itself to define a diameter only slightly larger than that of shaft 58. The lumen 64 opens interiorly of the balloon 94 so that by communication of pressurized fluid to the luer fitting 76 seen in FIG. 2A, the balloon 94 may be inflated to the dashed line condition of FIG. 2B. Conversely, by application of a subambient pressure to the fitting 76, the balloon 94 may be deflated to its smaller-diameter condition.

Intermediate of the bonds 96, 98, the shaft 58 carries a radiopaque marker 102 by which a physician can visualize the location of the balloon 94 preparatory to the dilation of a lesion by inflation of this balloon. It should be noted that at the bond 96, the shaft 58 includes a tubular single-lumen distal extension portion 58c, which is bonded to the remainder of this shaft at the bond 96. This single lumen extension portion 58c defines a respective bore 62a of diameter like the bore 62 of the dual lumen shaft portion 58, and coextensive therewith to extend the lumen of bore 62 to a distal opening 104. Circumscribing the distal opening 104, the shaft portion 58c carries a sleeve 106 of radiopaque material. For example, this sleeve 106 can be made from a mixture of tantalum and polyethylene. This sleeve 106 allows the physician to identify where the distal end of the shaft 58 is located.

Further considering FIG. 2B, it is seen that the distal end portion 92 of catheter shaft 58 defines a port 108 proximally of balloon 94, and a port 110 distally of the balloon 94, with both ports 108 and 110 opening into the bore 62. However, considering FIG. 3, it is clear that in the depicted position of the guide wire sheath 30 and guide wire 12, the lumen represented by bore 62 is substantially occupied by these assemblies and could not flow very much perfusion blood past the balloon 94.

Consequently, when a physician has positioned the balloon 94 at a lesion to be dilated, the physician withdraws the guide wire assembly 12 so that the tip 26 is about flush at end 24 with the distal end 38 of the guide wire sheath 30. This relative positioning of the guide wire 12 and shaft 32 can be visualized by the alignment of markers 26 and 40 (viewing FIG. 4).

Also, (still viewing FIG. 4) the physician withdraws the guide wire sheath 30 along with the guide wire 12 in the position just explained to a position illustrated wherein the end 38 is positioned proximally of the port 108. To facilitate such positioning of the guide wire sheath assembly, the shaft 32 can be provided with an external marker (not seen in the drawing Figures) which marker comes into alignment with the end 88 just outside of the luer fitting 90 when the end 38 is withdrawn into the shaft 58 of the catheter assembly 56 so that the ports 108 and 110 are both opened and communicate freely with one another via the lumen represented by bore 62. As FIG. 4 depicts, in this condition of the catheter 10, perfusion blood may flow via the ports 108 and 110 past the balloon 94, as is represented by arrows 112, and 114, to supply oxygenated blood to downstream tissues.

After the balloon 94 is again deflated, it may be desirable to dilate a further lesion located distally of the first lesion so that the catheter is required to be advanced further along the vessel under treatment. In this case, the sheath 30 and guide wire 12 are advanced together across the ports 108, 110 so that there is no chance of the guide wire tip 26 escaping the catheter 10 from one of the ports 108 or 110. Thus, both safety for the patient and certainty of placement of the catheter for the physician are improved by the simultaneous advancement of the guide wire 12 and the sheath 30 for this guide wire. Once the tip 26 is advanced distally of the ports 108, 110, the guide wire 12 may again be extended beyond the sheath 32 to facilitate further advancement of the catheter 10 and treatment of additional lesions, as described.

FIGS. 5–7 depict an alternative embodiment of the inventive catheter which is the same as the embodiment shown in FIGS. 1–5 with the exception of structural differences to be described. In the embodiment of FIGS. 5–7, the guide wire sheath 30 is itself configured to define a pilot catheter with a pilot balloon of small size which may be advanced, for example, into a tight lesion to initially dilate the lesion in preparation for further dilation with the balloon of the catheter itself. Consequently, the embodiment of the catheter shown in these Figures may allow a physician to open a tight lesion by the proper selection of guide wire sheath pilot balloon and catheter balloon sizes, and to thereby avoid exchanging a first catheter with a second catheter having a larger balloon. In order to obtain reference numerals for use on FIGS. 5–7, features depicted in these Figures which are analogous in structure or function to those features depicted and described above are referenced with the same numeral used previously, and having a prime added thereto.

Viewing FIGS. 5–7, it is seen that the guide wire sheath assembly 30' at a proximal end portion 116 thereof is provided with a Y-connector 118. This Y-connector 118 is provided with a branch inflation port 120 which at a luer fitting 122 may receive pressurized fluid into the bore 36' of the guide wire sheath assembly 30'. The Y-connector 118 is also provided with a compression sealing hub 124 which prevents loss of the pressurized fluid about the guide wire assembly 12'. A proximal portion 14' of the guide wire assembly is seen extending outwardly of the hub 124. When the hub 124 is loosened by use of a finger nut 126, the guide wire assembly 12' is freely movable axially and in rotation relative to the guide wire sheath 30'.

A distal end portion 128 (seen in FIG. 6) of guide wire sheath 30' at shaft 32' thereof includes a number of elements which are sequentially arranged axially along the length of the catheter 10' in this end portion 128. First, adjacent to the remainder of the shaft 32', and joined thereto at a bond 130 is an expandable dilatation balloon 132 (shown inflated). Next to the dilatation balloon 132 and integrally formed therewith is a cylindrical seal section 134 leading to the distal end 38' and defining the distal opening 36'. The balloon 132 is seen to include a side wall 136 which in a deflated condition is folded and over wrapped on itself to provide a comparatively small overall diameter. In fact, the outer diameter of the balloon 132 in its deflated condition is sufficiently small that the balloon can pass into the lumen 62' of catheter assembly 56' (viewing FIG. 7).

As is shown in FIG. 6, dilatation balloon 132 is formed as an integral part of guide wire sheath 30' in fluid communication with a single, axial lumen running throughout the length of tubular shaft 32' and defined by the bore 36' of this shaft. The guide wire assembly 12', as mentioned above, extends throughout the length of guide wire sheath assembly 30', and beyond distal end opening 36'. Distal orifice 36' is provided with seal means in the form of sleeve-like seal section 134. This seal section 134 includes a nonexpandable but resilient side wall portion 140 defining an inner surface 142 which is sealingly and releasably engaged by guide wire assembly 12' at a valving portion 144 thereof.

Viewing FIG. 6, it will be seen that in the exemplary embodiment of the present invention the means of valving portion 144 of guide wire assembly 12' which releasably engages the sleeve-like section 134 in sealing relationship is formed as a sleeve-like cylindrical collar 146 which is dimensioned to slidingly and sealingly engage into the sleeve-like seal section 134 with a light friction fit. That is, the collar 146 will pass through the seal section 134, in response to either a sufficient pulling or pushing force on guide wire assembly 12', but the collar 146 does not simply fall or slip through the seal section 134. This cylindrical collar 146 is sealingly and relatively rotatably coupled to guide wire 12', but is constrained from relative axial movement on the guide wire assembly 12' by a pair of retaining rings 148 and 150 respectively carried immovably on the guide wire assembly 12' proximally and distally of the collar 146. The retaining rings 148 and 150 may be welded or swaged onto the guide wire assembly 12', for example.

The sealing relationship of the collar 146 on the guide wire assembly 12' is established by the sealingly close fit of a cylindrical bore 152 through the collar member 146 on a cylindrical surface portion 154 of the guide wire assembly 12'. Because the collar member 146 is relatively long in relation to the diameter of the bore 152, and the fit between the bore 152 and surface 154 is close, fluid leakage axially through bore 152 is minimal. However, the fit of collar member 146 on surface portion 154 of the guide wire assembly 12' is such that the latter is substantially freely rotatable relative to the collar member.

This exemplary construction produces a releasably engaging seal which fixes guide wire assembly 12' removably in position relative to balloon 132, yet which allows guide wire 12' to be rotated freely without wrapping balloon 132 about the shaft 32, or guide wire 12'. Additionally, while the retaining collars are shown in FIG. 5 as being disposed immediately on each side of the collar 146, those ordinarily skilled in the pertinent arts will recognize that these collars 148 and 150, may be spaced somewhat from the collar 146 so that an added degree of sliding axial movement for the guide wire assembly 12' is provided without dislodging the sleeve-like collar 146 from sealing relation with the seal section 134. This added degree of axial movement for the guide wire 12' allows the physician to extend or retract the distal end portion 28' of guide wire assembly 12' relative to the distal end portion 128 of the guide wire sheath assembly 30' and shaft 32' thereof when necessary for steering and positioning of the catheter while still retaining the seal between collar 146 and seal section 134. As will be seen, the collar 146 can be disengaged from the seal section 134 by axial movement of the guide wire assembly 12'.

In FIG. 6, the solid lines depict balloon 132 inflated by a radiologically opaque or partially opaque contrast fluid. The radiopaque fluid allows the attending physician to place the balloon where desired with respect to an arterial lesion or stenosis. Also, as the dilatation balloon inflates, this enlargement in diameter of the balloon is visible to the physician who can thereby judge the extent to which the vessel is being enlarged. In the position of guide wire assembly 12' depicted in FIG. 6, the orifice 36' is sealingly closed by the collar member 146 in seal section 134. Consequently, the balloon 132 is inflated by the contrast fluid supplied thereto. By way of example only, the initial or uninflated diameter of balloon 132 may be on the order of about 0.5 mm, and its inflated diameter may be from about 1.5 mm. Thus, the balloon 132 may provide a ratio of diameter increase from its uninflated diameter to its inflated condition which in about 3:1, or more.

Subsequent to the inflation of dilatation balloon 132, the contrast fluid is withdrawn to deflate this balloon to its configuration seen in FIG. 7. Consequently, the main dilation balloon of the catheter 10 may be advanced into position across the lesion in order to further dilate the lesion. As will be easily understood in view of the explanation above of the embodiment depicted in FIGS. 1-4, the guide wire sheath 30' may be withdrawn into the catheter shaft 58' in order to allow full perfusion blood flow through this catheter shaft while the main dilation balloon is inflated. As was pointed out above, the balloon 132 in its deflated condition is sufficiently small to be received into the bore 62' of the catheter 10'. During this perfusion blood flow in the catheter 10', the guide wire assembly may be left in its position relative the sheath as is illustrated in FIG. 6, with the sheath sufficiently retracted in the catheter shaft to place the guide wire proximal of the ports 108' and 110'. Alternatively, as will be seen, the guide wire assembly 12' may be retracted into the guide wire sheath 30 so that the tip 26' is aligned with the end 38'. That is, the guide wire assembly is movable axially relative to the guide wire sheath 32' by movement of the sealing collar 146 out of or through the seal section 134.

FIG. 7 shows that the guide wire assembly 12 is subsequently advanced axially relative to the remainder of the catheter in order to open distal end port 36'. This opening of fluid communication through the lumen 36' and from the distal end 38' allows a treatment fluid, for example, a plaque solubilizing fluid, or a medicinal fluid (i.e., a drug, such as heparin) to be introduced via the luer fitting 122 of Y-connector 118.

FIGS. 8 and 9 cooperatively depict yet another alternative embodiment of the present invention. The features of the invention depicted in FIGS. 8 and 9 may be employed with either of the alternative embodiments of the invention depicted in FIGS. 1-7. Consequently, the catheter structure of the embodiment of the invention shown in FIGS. 8 and 9 is only fragmentarily set forth, the remainder of the structure being understood as being the same as that depicted and described earlier herein. Again, in order to obtain reference numerals for use in describing the structure and function of the embodiment of the invention depicted in FIGS. 8 and 9, features of the invention which are analogous in structure or function to those depicted and described earlier herein are referenced with the same numeral used before and having a prime added thereto. In instances where the addition of a prime to a numeral used above would result in a double prime, the second prime is dropped, and the reader will understand that the same or equivalent structure or function is intended.

Viewing FIG. 8, a catheter 10' is seen to include a guide wire sheath assembly 30' which proximally extends from the proximal end of the catheter shaft assembly 56' via a Y-connector 66'. The guide wire sheath assembly includes a flexible distal portion 32' which is equivalent in structure and function to the guide wire sheath depicted and described in connection with FIGS. 1-3.

The guide wire sheath assembly 30' also includes a proximal end portion 32a which is of only limited flexibility. This proximal end portion 32a is defined by a length of small diameter metallic tubing 156 which is joined to the flexible portion 32' of shaft 30' at a bond 158. A proximal end portion 160 of the tubing 156 defines a slot 162 laterally from which extends the proximal end portion 14' of the guide wire assembly 12'. At a proximal end 164 of the tubing 156, the latter defines an axial opening 166 leading to a guide wire end coupling feature, which is generally referenced with the numeral 168.

While a variety of alternative structures are possible for the guide wire coupling feature 168, the preferred structure includes at least one reduced diameter groove 170 swaged into the end portion of tubing 156, and an axially spaced end swage 172 cooperatively retaining at least one resilient snap ring member 174 within the end coupling feature 168 immediately inwardly of opening 166. Preferably, the snap ring member 174 may be made as a resilient elastomeric O-ring member.

Further, the proximal end portion 14' of guide wire assembly 12' includes a proximal end guide sheath coupling feature, which is generally referenced with the numeral 176. This guide sheath coupling feature 176 includes a conical end portion 178 of the guide wire assembly 12', which end 178 may be inserted through the opening 164 to be introduced into the O-ring member 174. The conical end portion 178 leads to a capture groove 180 into which the O-ring member 174 is receivable to retain the proximal end 14' of guide wire assembly 12' in engagement with the proximal end 160 of guide wire sheath assembly 30'.

Consequently, a physician who wishes to withdraw the catheter shaft assembly 56' in order to replace this catheter, for example, with a catheter having a larger balloon, does not have to obtain a guide wire extension. The guide wire assembly 12' of the present invention is simply withdrawn from the patient leaving the guide wire sheath 30 in the patient as a guide over which the new balloon catheter may retrace the route back to the vessel under treatment. The guide wire 12' at its proximal end 176 is attached to the proximal portion of the guide wire sheath assembly 30' to serve as a guide wire extension. That is, the guide wire assembly 12' is turned end-for-end and connected with the proximal end of the guide wire sheath assembly 30'.

With the guide wire sheath and guide wire assembly so connected, as is fragmentarily illustrated in FIG. 9, the catheter shaft assembly 56' may be withdrawn along the guide wire sheath and guide wire, as is indicated by the arrow 182. This withdrawal of the catheter shaft assembly 56' leaves the guide wire sheath assembly 30' in place to serve as a guide member for retracing the path back to the vessel under treatment. It will be noted that the guide wire assembly itself is reversed in its proximal and distal end orientations with respect to the patient in its use as an extension for the guide wire sheath assembly 30'. However, such reversal need not be the case. If desired, a coupling feature may be provided near the distal end of the guide wire so that this feature couples with the proximal end coupling feature 168 of the guide wire sheath assembly 30'.

Alternative coupling features may be employed to couple the guide wire sheath assembly and guide wire assembly at adjacent ends thereof so that the latter may serve as an extension of the former. For example, one of these assemblies could define a threaded axial end bore, while the other defines a threaded axial end stem which is threadably engageable with the end bore of the other member. Still alternatively, a coupling similar to a turn buckle structure could be defined between the guide wire assembly and guide wire sheath assembly. Another alternative is to define a small scale collar at the proximal end of the guide wire sheath assembly, and to lock an end of the guide wire assembly in this collar with a small set screw. An equivalent structure would involve the formation of a small scale collet structure at the proximal end of the guide wire sheath assembly, and the locking of an end of the guide wire assembly in this collet structure.

As noted above, the exchangeable balloon catheter of the present invention enables a vascular physician to exchange one catheter for a second catheter along the prepositioned guide wire sheath assembly without having to retrace the entire vascular pathway with a new guide wire. Thus, the balloon catheter can be replaced with a catheter having a balloon provided with a different expandable diameter if necessary to reopen a particularly difficult stenotic lesion. Similarly, if problems develop with the inflation of balloon 94 during angioplasty it is possible to replace the balloon with a properly functioning device. All the vascular physician need do is to retract the guide wire shaft 18, attach this shaft as an extension of the guide wire sheath which has been left in place, and withdraw the catheter shaft assembly. A new catheter shaft assembly can be inserted to retrace the path to the end of the guide wire sheath assembly, and the guide wire then can be reinserted into the guide wire sheath. As those skilled in the pertinent art will appreciate, this placed guide (in the present instance, a guide wire sheath assembly) greatly facilitates the speed and safety of such a catheter replacement procedure.

FIG. 10 depicts another alternative embodiment of the present invention, which is similar to the embodiment illustrated in FIGS. 5-7, with the exception that the embodiment of FIG. 10 has additional features which allow the catheter to be used in a mono-rail configuration. In order to obtain reference numerals for use on FIG. 10, features of the depicted embodiment which are analogous in structure or function to features depicted and described above are referenced with the same numeral used above, but having a prime added thereto.

Viewing FIG. 10, the catheter 10' includes an elongate catheter shaft assembly 56', which includes a comparatively rigid metallic hypo-tube proximal portion 184, and a flexible dual-lumen distal portion 58'. The distal portion 58' includes an inflation lumen 64' (not visible in the drawing Figure) connecting to a balloon section 94'. Adjacent the proximal end 186 of distal portion 58', the hypo tube portion 184 is bonded in communication with lumen 64'. At its proximal end 190, the hypo tube portion 184 carries a luer fitting 192. As is understood, the balloon section 94' can be inflated and deflated by the application of positive and negative fluid pressures, respectively, at the fitting 192.

In a distal end portion 92' of the catheter 10', the side wall 60' defines both proximal 108, and distal 110' perfusion ports. As will be well understood, these ports 108', 110' allow perfusion blood to flow past the inflated balloon section 94'. However, spaced proximally from the most proximal extent of the proximal perfusion ports 108, the side wall 60' defines an aperture 194 from which a proximal portion 196 of the guide wire sheath 30, including a proximal portion of the guide wire assembly 12', extends outwardly from the lumen 62'. Proximally of the aperture 194, the sheath 30 and guide wire 12' extend outwardly of the shaft 56'. However, distally of the aperture 194 and extending to distal opening 104', the shaft portion 58' defines a mono-rail guide portion 198. This mono-rail guide portion 198 receives, and is slidable along, the sheath 30' in the lumen 62'.

Consequently, the catheter shaft 58' may be retracted along the sheath 30' without the need for a guide wire extension because a proximal end portion 196 of the sheath 30' is exposed and accessible to retain location of the sheath in the patient under treatment. That is, the sheath 30' acts as a guide member for retraction of the catheter shaft 58'. Of course, a replacement catheter can then retrace the route back to the treatment site along the guide sheath 30'.

Importantly, distally of the aperture 194 and proximally of the most proximal extent of the perfusion ports 108', the distal end portion 92' of the catheter 10' defines an elongate sheath retention portion 200. This sheath retention portion 200 is a proximal part of the guide portion 198.

As will be easily understood in view of the explanation above, when the balloon section 94' is inflated to dilate a lesion, the guide sheath 30' and guide wire assembly 12' are drawn back so that their distal ends 24' and 38' are both at least slightly proximal of the perfusion port 108'. This positioning for the sheath and guide wire allows the entire cross sectional area of the lumen 62' to be used for perfusion blood flow.

However, it is important that the sheath and guide wire at their distal and portions be retained within the catheter shaft 58' in the retention portion 200 thereof, and not be withdrawn entirely through the aperture 194. Consequently, after the dilation of balloon section 94', should the physician wish to again advance the guide wire 12' and sheath 30' (perhaps to guide the entire catheter to another deeper lesion), then these components can again be advanced through the mono-rail guide portion 198.

It also should be emphasized that the axial lumen represented by bore 62 of the present invention is configured to perform a dual role. On the one hand, this lumen serves as a guide wire lumen, receiving both the guide wire 12, and guide wire sheath 30. On the other hand, this lumen 62 serves as a perfusion blood flow passage allowing perfusion blood to bypass the inflated dilatation balloon 94. Because the guide wire and its sheath are withdrawn at their distal ends to a position proximal of the perfusion ports of the catheter, the entire cross sectional area of the guide wire and perfusion lumen is available for perfusion blood flow. Still, when the guide wire is to be advanced distally of the perfusion ports, for example, in order to allow additional advancing movement of the catheter 10 along the guide wire, the guide wire sheath is advanced to prevent the distal end of the guide wire from escaping the catheter lumen via the perfusion ports. Thus, the safety of the procedure for the patient is improved. This multifunctional catheter design produces an ultra-low profile device which significantly enhances its ability to cross very tight stenoses or to traverse particularly difficult vascular pathways.

Along these lines, exemplary non-limiting dimensions for the balloon catheter assembly of the present invention may be as follows. For example, as is typical in the coronary arts, the overall length of catheter 30 will typically range from 120 cm to 160 cm. The axial length of the dilatation balloon 94 will comprise approximately 1 cm to 4 cm of this overall length. Typically, dilatation balloons are available in stepped dilatation diameters ranging from approximately 0.5 mm to 5.0 mm, in 0.5 mm or 0.25 mm increments. As known in the art, these inflation diameters are typically achieved at 6 to 10 atmospheres of pressure. Naturally, the deflated profile of the dilatation balloons increases slightly with the final dilatation diameter. Exemplary non-limiting diameters for the proximal portion of guide wire 12 range from 0.005 to 0.016 inches whereas the preferred exemplary outer diameter for the cylindrical collar 146 ranges from approximately 0.012 to 0.020 inches. Thus, in the embodiments of the present invention illustrated the drawing Figs., the distal end portion of guide wire assembly 12 is provided with a cross-sectional diameter on the order of approximately 0.005 inches and cylindrical collar 146 is formed of a polymeric material such as PTFE having an outer diameter of approximately 0.016 inches and a wall thickness of approximately 0.005 inches.

It should be emphasized that the proximal diameter of guide wire assembly 12 need not be constant and may taper to provide an enhanced degree of flexibility toward the distal end of guide wire assembly. Guide wire assembly 12 itself is preferably formed of metal such as stainless steel but also may be constructed of polymers or polymer coated metals as is known in the art. An exemplary overall wire length for guide wire assembly 12 is on the order of 175 cm. The cross section of guide wire assembly 12 distal of the cylindrical collar 146 need not be circular to be within the scope of the present invention.

Although not essential to the practice of the present invention, guide wire assembly 12 is preferably provided at flexible distal spring coil 24 with a smooth hemispherical radiopaque tip 26 in order to reduce vascular trauma and provide visualization as guide wire assembly 12 is advanced along a vascular pathway. Spring coil 24 may be formed of any resilient material, preferably metal, and in the preferred embodiment of the present invention is formed of a radiopaque material such as platinum or gold. Thus, spring coil 24 with tip 26 functions as an additional marker to assist the physician in positioning the apparatus of the present invention.

Though spring coil 24 is illustrated in the drawing Figs. as being relatively straight, it is commonly known in the art to precurve spring coil 24 so that the implanting physician can rotate wire assembly 12 and direct tip 26 of wire coil 24 into specific vascular junctions to direct the entire assembly along the proper pathway. Rotational manipulation of wire 12, or "torquing" as it is referred to in the art, is accomplished by rotating the proximal end portion 14 of the guide wire assembly. As is well known in the art, this rotation may be achieved with use of a variety of clamps or chuck devices which provide the physician with purchase on the wire 12. The axially flexible construction of guide wire 12 transmits this torque along the entire longitudinal extent of wire 12 to coil 24. However, because cylindrical collar 146 is preferably sealingly coupled to guide wire 12 in a relatively rotatable manner, this torque is not transmitted to balloon 132, and prevents this balloon from wrapping in a spiral fashion around guide wire 12.

Thus, the apparatus of the present invention according to one alternative embodiment thereof provides an exchangeable integrated-wire perfusion balloon catheter that can be positioned within a vascular pathway by a single physician. Because the apparatus of the present invention provides the maneuverability of a fixed-wire dilatation catheter coupled with the benefits of an ultra-low catheter profile it can be quickly and easily maneuvered into position across lesions that are critically narrowed and irregularly shaped. Further, the distal end of its guide wire sheath may be left in place and the shaft of the guide wire itself may be used as an extension to the guide wire sheath so that the shaft of the catheter can be retracted back from the lesion to allow the surgeon to retain a guide member across the lesion. Alternatively, while leaving the guide member in place the surgeon can completely remove and replace the balloon catheter with one having alternative dimensions.

Flexible tubular shaft 32 and catheter shaft 56 are preferably formed of a polymeric material such as polyethylene, polyamide, polyimide, polypropylene, polyvinyl, polyester such as polyethyleneterephthalate (PET), or polyolefin copolymer. Additionally, to improve its lubricity, shaft 32 may be coated with PTFE, silicone or other materials including low friction lubricants.

Similarly, low friction coatings such as PVC, polyamide or fluoropolymer or such as PTFE or hydrophilic materials and lubricants may be utilized to enhance the movement of all components of catheter 10 during angioplasty. Resilient sleeve-like seal section 138 may be formed from the same material forming the remainder of tubular shaft 32, or it may alternatively be formed from a lubricous polymeric material. Alternatively, resilient sleeve 138 may be coated along its inner surface with a lubricous material to facilitate its engagement with cylindrical collar 146.

Cylindrical collar 146 similarly can be formed of a wide variety of materials ranging from stainless steel to polymeric materials and may even be formed as an integral part of guide wire assembly 12. However, it is preferred that collar 146 be formed of a polymeric material such as PVC, polyamide, polyimide, or fluoropolymer such as polytetrafluoroethylene (PTFE) as this provides an added degree of flexibility to the guide wire assembly 12 within the distal end portion 128 of the catheter 10.

In closing it is to be understood that the embodiments of the invention disclosed herein are illustrative of the principals of the invention and that other modifications may be employed which are within the scope thereof. Thus, by way of example, but not of limitation, the seal section 138 may be configured to extend into the dilatation balloon as opposed to the depicted configuration in which this seal section extends outwardly of the balloon portion. Accordingly, the present invention is not limited to that precisely as shown and described in the specification.

What is claimed:

1. A dual-lumen perfusion balloon catheter comprising a dual-lumen catheter shaft, said catheter shaft at a distal end portion thereof carrying an expansible balloon section, an inflation lumen of said dual-lumen catheter shaft communicating internally of said balloon section, a guide wire and perfusion lumen of said catheter shaft traversing said balloon section, a pair of perfusion ports respectively located proximally and distally of said balloon section and both opening outwardly from and communicating with one another via said guide wire and perfusion lumen, a guide wire assembly including a distal end portion movably received in said guide wire and perfusion lumen and traversing said balloon section, and a tubular guide wire sheath member movably received in said guide wire and perfusion lumen and receiving said guide wire to traverse said perfusion ports while positively preventing said guide wire distal end portion from escaping the catheter via said perfusion ports.

2. The catheter of claim 1 further including said guide wire sheath member carrying a respective balloon member adjacent to a distal end thereof, said balloon member of said guide wire sheath member being of a diameter sufficiently small to pass into said guide wire and perfusion lumen proximally of said balloon section.

3. The catheter of claim 2 wherein said guide wire sheath member includes a seal section located distally of said balloon member, and said guide wire includes a valving collar sealingly receivable into said seal section to allow inflation of said balloon member by communication of pressurized fluid to said guide wire sheath member at a proximal end thereof.

4. The catheter of claim 3 wherein said valving collar includes a sleeve of polymeric material rotatably received on said guide wire in said distal end portion thereof with selected relative axial movement on said guide wire.

5. The invention of claim 4 wherein said polymeric material is selected from the group comprising:
   polyvinylchloride, polyamide, polyimide and fluoropolymer.

6. The invention of claim 3 wherein said valving collar is formed of metal.

7. The invention of claim 1 further comprising at least one radiopaque marker disposed adjacent to said distal end portion of said guide wire.

8. The invention of claim 7 wherein said radiopaque marker comprises a flexible metallic coil defining at least a part of said distal end portion of said guide wire.

9. The invention of claim 1 wherein said catheter shaft distal end portion defines an aperture opening outwardly from said guide wire and perfusion lumen, said distal end portion of said catheter shaft defining a mono-rail guide portion distally of said aperture.

10. The invention of claim 9 wherein said catheter shaft further defines an elongate guide wire sheath retention portion distally of said aperture and proximally of a proximal one of said pair of perfusion ports.

11. The invention of claim 10 wherein said catheter shaft further includes a proximal metallic hypo tube portion joining with a distal comparatively more flexible portion of said catheter shaft.

12. The invention of claim 1 wherein said guide wire sheath member and said guide wire assembly define cooperating means for joining a proximal end portion of said guide wire sheath member with an end of said guide wire assembly in end-to-end relation.

13. The invention of claim 12 wherein said cooperating means for joining includes said guide wire sheath member at a proximal end thereof carrying a resilient elastomeric member, said elastomeric member defining an opening into which an end of said guide wire assembly is insertable, and said guide wire assembly adjacent an end thereof defining a circumferential groove and an adjacent conical end surface portion allowing said end of said guide wire to be introduced forcefully into said opening of said elastomeric member so that the latter is received into said groove.

14. The invention of claim 1 wherein said catheter shaft and said expandable balloon section are formed of resilient polymeric material.

15. The invention of claim 14 wherein said polymeric material is selected from the group comprising homopolymers and copolymers of:
polyvinylchoride, polyethylene, polyolefin, fluoropolymer, polyamide, polyester, polyimide, and polypropylene.

16. A low-profile dual-lumen dual-balloon catheter and guide wire combination comprising:
a flexible, small diameter guide wire assembly having proximal and distal ends, with a valving portion of said distal end being of a larger diameter than the remainder of said guide wire;
a flexible elongated tubular guide wire sheath having a proximal end and a distal end and a single axially extending fluid-conducting lumen adapted to receive said guide wire extending therethrough and opening on a distal end of said guide wire sheath;
a balloon member disposed at a distal end portion of said guide wire sheath and in fluid communication with said lumen of said guide wire sheath, said distal opening of said guide wire sheath being provided with means for releasably engaging said enlarged diameter distal end valving portion of said guide wire assembly in sealing relationship;
a catheter shaft having a pair of lumens extending therein, one of said pair of lumens slidably receiving said guide wire sheath and defining a distal end opening through which respective distal end portions of said guide wire and guide wire sheath are extendably distally of said catheter shaft,
a balloon section carried on a distal end portion of said catheter shaft, and the other of said pair of lumens communicating with said balloon section; and
a side wall of said catheter shaft defining a pair of perfusion ports respectively located distally and proximally of said balloon section;
whereby said guide wire and sheath are retractable proximally of a proximal one of said pair of perfusion ports to allow perfusion blood flow through the full cross sectional area of said one catheter shaft lumen, and said guide wire sheath and guide wire together may be advanced across said perfusion ports while said sheath positively prevents escape of a distal end portion of said guide wire from said catheter shaft via said perfusion ports.

17. The invention of claim 16 wherein said larger diameter guide wire distal end valving portion is defined by a cylindrical collar member coupled to said guide wire distal end portion for relative rotational movement and a selected axial relative movement.

18. The invention of claim 16 wherein said means for releasably sealingly engaging said enlarged diameter distal end portion of said guide wire is a resilient sleeve-like seal portion of said guide wire sheath balloon member which extends from said distal opening thereof.

19. The invention of claim 18 wherein said resilient sleeve-like seal portion is formed from a lubricous polymeric material.

20. The invention of claim 16 wherein said catheter shaft and said balloon section are formed of resilient polymeric material.

21. In a medical treatment catheter including an elongate catheter shaft defining a guide wire and perfusion lumen extending therein, the guide wire and perfusion lumen receiving a guide wire assembly which in a first position thereof extends distally of a distal end of said catheter shaft, the catheter shaft at a distal end portion thereof carrying an inflatable dilatation balloon, the catheter shaft defining a pair of perfusion ports opening outwardly from said guide wire and perfusion lumen each on respective opposite distal and proximal sides of the dilatation balloon, the guide wire assembly being retractably proximally of said pair of perfusion ports to allow perfusion blood flow via the entire cross sectional area of said guide wire and perfusion lumen while said dilatation balloon is inflated, a method of preventing escape of a distal end of said guide wire from said catheter shaft via said pair of perfusion ports, said method comprising the steps of:
providing a tubular guide wire sheath member receivably into said guide wire and perfusion lumen;
disposing said guide wire assembly in said tubular guide wire sheath member;
disposing said guide wire assembly and said guide wire sheath member together in said guide wire and perfusion lumen so that a distal end of said guide wire is extended beyond a distal end of said catheter shaft to guide advancement of said catheter;
retracting said guide wire sheath member and said guide wire together proximally of said pair of perfusion ports to allow perfusion blood flow via the full cross sectional area of said guide wire and perfusion lumen when said dilatation balloon is inflated; and
advancing said guide wire sheath and said guide wire assembly together across said pair of perfusion ports so that said guide wire sheath member positively prevents escape of a distal end portion of said guide wire assembly through said perfusion ports.

22. In a medical treatment catheter including an elongate catheter shaft defining a guide wire and perfusion lumen extending therein, the guide wire and perfusion lumen slidably receiving a guide wire assembly which in a first position thereof extends distally of a distal end of said catheter shaft, the catheter shaft at a distal end portion thereof carrying an inflatable dilatation balloon, the catheter shaft defining a pair of perfusion ports opening outwardly from said guide wire and perfusion lumen each on respective opposite distal and proximal sides of the dilatation balloon, the guide wire assembly being retractably proximally of said pair of perfusion ports to allow perfusion blood flow via the entire cross sectional area of said guide wire and perfusion lumen while said dilatation balloon is inflated, a method of providing an extension of a guide member so that said catheter shaft may be retracted along said guide member and said extension together in preparation for the retracing along said extension and guide member of another subsequent catheter shaft to a treatment site, said method comprising the steps of:

providing an elongate tubular guide wire sheath member slidably receivably into said guide wire and perfusion lumen;

slidably disposing said guide wire assembly in said tubular guide wire sheath member;

at a proximal end of said guide wire sheath member and at an end portion of said guide wire assembly providing cooperating engagement means for joining said guide wire assembly and said guide wire sheath member together in end-to-end relation;

withdrawing said guide wire assembly from said guide wire sheath member while retaining the latter in place at a treatment site;

joining together said guide wire sheath member and said guide wire assembly externally of a patient under treatment so that said guide wire assembly defines said extension of said guide wire sheath member; and employing said guide wire assembly as an extension of said guide wire sheath for retraction of said catheter shaft while retaining said guide wire sheath member at said treatment site.

* * * * *